United States Patent [19]

Therriault et al.

[11] Patent Number: 5,573,778
[45] Date of Patent: Nov. 12, 1996

[54] DRUG FLUX ENHANCER-TOLERANT PRESSURE SENSITIVE ADHESIVE COMPOSITION

[75] Inventors: Donald J. Therriault; Kenneth W. Rodgers, both of York, Pa.

[73] Assignee: Adhesives Research, Inc., Glen Rock, Pa.

[21] Appl. No.: 405,872

[22] Filed: Mar. 17, 1995

[51] Int. Cl.⁶ .................................................. A61F 13/02
[52] U.S. Cl. ............................................ 424/448; 424/449
[58] Field of Search ....................................... 424/448, 449

[56] References Cited

U.S. PATENT DOCUMENTS

| | | | |
|---|---|---|---|
| 3,786,116 | 1/1974 | Milkovich et al. | 525/276 |
| 3,832,423 | 8/1974 | Milkovich et al. | 525/286 |
| 3,842,146 | 10/1974 | Milkovich et al. | 525/271 |
| 3,862,077 | 1/1975 | Schulz et al. | 524/417 |
| 3,879,494 | 4/1975 | Milkovich et al. | 525/85 |
| 3,928,255 | 12/1975 | Milkovich et al. | 521/134 |
| 3,989,768 | 11/1976 | Milkovich et al. | 525/130 |
| 4,085,168 | 4/1978 | Milkovich et al. | 525/59 |
| 4,551,388 | 11/1985 | Schlademan | 428/355 |
| 4,554,324 | 11/1985 | Husman et al. | 525/301 |
| 4,656,213 | 4/1987 | Schlademan | 524/272 |
| 4,693,776 | 9/1987 | Krampe et al. | 156/327 |
| 4,732,808 | 3/1988 | Krampe et al. | 428/355 |
| 4,871,812 | 10/1989 | Lucast et al. | 525/186 |
| 4,973,468 | 11/1990 | Chiang et al. | 424/449 |
| 4,994,267 | 2/1991 | Sablotsky | 424/78 |
| 5,053,227 | 10/1991 | Chiang et al. | 424/448 |
| 5,059,426 | 10/1991 | Chiang et al. | 424/449 |
| 5,151,271 | 9/1992 | Otsuka et al. | 424/443 |
| 5,175,052 | 12/1992 | Tokuda et al. | 428/355 |
| 5,176,916 | 1/1993 | Yamanaka et al. | 424/448 |
| 5,200,190 | 4/1993 | Azuma et al. | 424/443 |
| 5,262,165 | 11/1993 | Govil et al. | 424/448 |
| 5,352,516 | 10/1994 | Therriault et al. | 428/355 |
| 5,368,860 | 11/1994 | Sunami et al. | 424/448 |
| 5,372,819 | 12/1994 | Godbey et al. | 123/238 |

OTHER PUBLICATIONS

Pfister, William R. et al., Permeation Enhancers Compatible with Transdermal Drug Delivery Systems Part 1: Selection and Formulation Considerations, Pharmaceutical Technology, pp. 132–140, Sep. 1990.

Pfister, William R. et al., Permeation Enhancers Compatible with Transdermal Drug Delivery Systems Part II: System Design Considerations, Pharmaceutical Technology, Oct. 1990.

*Primary Examiner*—D. Gabrielle Phelan
*Attorney, Agent, or Firm*—Jones, Tullar & Cooper, P.C.

[57] ABSTRACT

A drug flux enhancer-tolerant pressure sensitive adhesive composition is provided comprised of a mixture of (1) a percutaneous penetration enhancer to increase permeability of skin to transdermally administered pharmacologically active agents and (2) a macromer reinforced base polymer, said base polymer comprising a phase separated graft copolymer composition comprised of copolymerized monomers A and B to form a backbone polymer having polymeric moieties grafted thereto, wherein monomer A is a monomeric acrylic or methacrylic ester of a non-tertiary alcohol having from 1 to 14 carbon atoms, with the average number of carbon atoms being in the range of about 4 to 12, and a monomer B is a polar monomer which is copolymerizable with monomer A.

15 Claims, No Drawings

DRUG FLUX ENHANCER-TOLERANT PRESSURE SENSITIVE ADHESIVE COMPOSITION

BACKGROUND OF THE PRESENT INVENTION

The present invention is directed to a pressure sensitive adhesive composition useful in transdermal administration of pharmacologically active agents.

The transdermal delivery of therapeutic agents has been the subject of intense research and development for over 20 years. These efforts have resulted in the creation of several commercially successful products whose advantages over other dosage forms are well documented.

The skin, however, is an exceptionally well designed barrier. As a result, only a relatively small number of drug molecules are suitable for transdermal delivery.

Various techniques have been explored in an attempt to enhance the permeation of compounds which are not otherwise suitable for transdermal delivery. The most promising approaches have been found to be iontophoresis, electroporation, sonophoresis, and chemical enhancement. Of these methods, chemical enhancement is the more established, and is currently commercially employed.

Chemical enhancers, or percutaneous penetration enhancers, have a broad spectrum of chemical structure depending on the application in which they are to be employed. The most common enhancers belong to the following groups: non-ionic surfactants, alcohols, fatty acid esters, and amines.

In order for enhancers to function properly, they must be present at the skin/device interface in sufficiently high quantity (generally 5–40% percent by weight based on the weight of the adhesive). As most transdermal drug delivery devices utilize pressure sensitive adhesives as a means of providing intimate contact between the drug delivery means and the skin, it is essential that the adhesive polymer be compatible with the specific enhancer used. In this way, adequate concentrations of the enhancer can be achieved by proper formulation with the adhesive without disrupting the physical integrity of the adhesive.

Polyacrylates are well suited to obtain the desired compatibility in that the polarity of the pendant moieties can be altered to accommodate the structure of the enhancer. Unfortunately, it is generally observed that when enhancers are compounded with these adhesives, the compatibility may be too great, resulting in dramatic reduction in the cohesive strength of the adhesive system.

To reduce the loss of adhesive integrity, attempts have been made to cross-link the adhesive polymers. Although this does increase the cohesive strength, the adhesive often does not possess sufficient flow to allow for long term adhesion to skin.

Clearly, then, the proper balance of enhancer compatibility, cohesive strength, and polymer flow is required for properly designed adhesive/enhancer systems.

Polymeric compositions are known which are comprised of backbone polymers having grafted thereto pendant polymeric moieties. The type of backbone polymer and graft polymeric moiety employed varies depending upon the desired characteristics of the end product. See, for example, U.S. Pat. Nos. 3,786,116; 3,832,423; 3,842,146; 3,862,077; 3,879,494; 3,928,255; 3,989,768; 4,085,168; 4,551,388; 4,554,324; 4,656,213; 4,693,776; 4,732,808; 4,871,812; and 5,352,516. These patents disclose various types of such polymers which may or may not exhibit pressure sensitive adhesive properties.

Typical of the type of polymeric compositions disclosed in the above patents are compositions comprised of a backbone polymer such as an acrylic or methacrylic backbone polymer having attached thereto a graft polymer comprised of a polymerizable macromolecular monomer such as styrene or alpha-methylstyrene. See, for example, U.S. Pat. No. 4,554,324, and commonly-assigned U.S. Pat. No. 5,352,516, among others, in this regard.

The acrylic pressure sensitive adhesives such as described in U.S. Pat. No. 4,554,324 and U.S. Pat. No. 5,352,516 may be made from an acrylic ester and a polar acrylic monomer. The polar acrylic monomer can be one or a mixture of acrylic acid, acrylamide, acrylonitrile, itaconic acid, etc. The acrylic ester can be any aliphatic ester of acrylic acid. Such monomers are typically polymerized free radically by solution, suspension or emulsion polymerization. The acrylate portion of the copolymer is generally present in a generally high concentration and renders the polymer tacky. The polar monomer increases the ability of the adhesive to bond to a surface.

U.S. Pat. Nos. 4,693,776 and 4,732,808 also disclose a pressure sensitive skin adhesive composition comprised of a macromer-reinforced acrylate copolymer. U.S. Pat. No. 4,871,812 discloses a moldable medical adhesive comprising a blend of an acrylate terpolymer adhesive containing a hydrophilic macromer moiety, and a reinforcing material which is a carbonylamido group containing polymer. U.S. Pat. No. 4,656,213 is directed to an acrylic hot melt pressure sensitive adhesive comprising a polyacrylate graft copolymer which may be plasticized to enhance the adhesive properties thereof.

Such adhesives have been found to suffer from the disadvantage that their adhesive properties are not sufficiently compatible with the skin (due to inadequate long-term tack) with the result that adhesive failure may occur after a short time due to movement of the skin.

It has accordingly been that reinforcement of the adhesive through the use of graft polymeric moieties or macromers, followed by plasticization with conventional percutaneous penetration enhancers, allows for the desired level of cohesiveness while allowing for a degree of adhesive flow which is essential for long term adhesion to skin.

OBJECTS AND SUMMARY OF THE INVENTION

It is therefore the object of the present invention to provide a pressure sensitive adhesive composition which possesses good compatibility with typical percutaneous penetration enhancers while maintaining the appropriate viscoelastic characteristics for adequate skin adhesion.

It is further an object of the present invention to provide a pressure sensitive adhesive composition into which may be incorporated large amounts of a percutaneous penetration enhancer without disadvantage.

In accordance with the present invention, there is thus provided a drug flux enhancer-tolerant pressure sensitive adhesive composition comprised of (1) a percutaneous penetration enhancer to increase permeability of skin to transdermally administered pharmacologically active agents and (2) a macromet reinforced base polymer, said base polymer component comprising a phase separated graft copolymer composition comprised of copolymerized monomers A and B to form a backbone polymer having polymeric moieties grafted thereto, wherein monomer A is a monomeric acrylic or methacrylic ester of a non-tertiary alcohol having from 1 to 14 carbon atoms, with the average number of carbon atoms being in the range of about 4 to 12, and monomer B is a polar monomer which is copolymerizable with monomer A.

In accordance with the present invention, there is also provided a transdermal drug delivery system for administering at least one pharmacologically active agent comprising a flexible backing material impermeable to said active agent and an adhesive layer on at least a portion of said backing material, the improvement wherein said adhesive layer comprises a pressure sensitive adhesive composition comprised of (1) a percutaneous penetration enhancer to increase permeability of skin to the transdermally administered pharmacologically active agent and (2) a macromer reinforced base polymer, said base polymer component comprising a phase separated graft copolymer composition comprised of copolymerized monomers A and B to form a backbone polymer having polymeric moieties grafted thereto, wherein monomer A is a monomeric acrylic or methacrylic ester of a non-tertiary alcohol having from 1 to 14 carbon atoms, with the average number of carbon atoms being in the range of about 4 to 12, and monomer B is a polar monomer which is copolymerizable with monomer A.

DETAILED DESCRIPTION OF THE INVENTION

The present invention pertains to a pressure sensitive adhesive composition comprised of a mixture of a percutaneous penetration enhancer and a phase-separated graft copolymer as well as transdermal drug delivery devices utilizing such a composition.

Specifically, the phase separated graft copolymer is comprised of copolymerized monomers A and B to form a backbone polymer having a polymeric moiety grafted thereto, wherein monomer A is a monomeric acrylic or methacrylic acid ester of a non-tertiary alcohol having from 1 to 14 carbon atoms with the average number of carbon atoms being in the range of about 4 to 12, and monomer B is a polar monomer which is copolymerizable with monomer A.

Exemplary A monomers include but are not limited to esters of acrylic acid or methacrylic acid with non-tertiary alcohols such as 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, 1-dodecanol, etc. Such monomers are known to those skilled in the art.

Exemplary B monomers include but are not limited to one or more of acrylic acid, methacrylic acid, itaconic acid, acrylamide, methylacrylamide, acrylonitrile, methacrylonitrile, diacetone acrylamide, and 2-carboxyl ethyl esters of acrylic acid.

The A monomer will generally be present in the copolymer in an amount with the range of from about 50 to 80 percent by weight, based on the total weight of the copolymer, with any additional monomers employed (such as the B monomer) and the polymeric graft moiety comprising the remaining portion of the copolymer. Further, the graft polymeric moiety will generally comprise from about 2 to 30 percent by weight of the combined amount of the B monomer and the graft polymeric moiety.

Preferably, the polymer graft is a polymeric moiety having a Tg greater than 20° C.

The composition of the present invention successfully overcomes the deficiencies of prior art adhesive compositions by providing for the presence of graft polymeric moieties while also providing for the presence of graft polymer chains in an amount sufficient to provide a reinforcing function which inhibits or restricts flow of the polymer backbone in the presence of the enhancer and/or in the presence of water (such as moisture on the skin).

The copolymer of the present invention is characterized as being "phase-separated". That is, the backbone of the copolymer and the attached graft are incompatible and thus do not mix together to form a homogeneous phase. Instead, the copolymer backbone forms a continuous phase within which is dispersed the attached graft phase. The dispersed graft discontinuous phase thus acts to mechanically reinforce the continuous phase.

The polymer graft may be attached to the polymer backbone by conventional techniques such as (1) copolymerization with the respective monomers of the backbone polymer (i.e., monomers A and B together with graft polymeric monomer moiety C) or (2) attachment of the polymeric graft moiety to a preformed backbone polymer via a suitable functional group subsequent to formation of same by copolymerization of monomers A and B.

With regard to technique (1) which comprises the preferred technique, the copolymer of the present invention may be formed from copolymerized monomers A, B and C, wherein (1) monomer A is a monomeric acrylic or methacrylic acid ester of a non-tertiary alcohol, said alcohol having from 1 to 14 carbon atoms with the average number of carbon atoms being in the range of about 4 to 12, (2) monomer B is a polar monomer copolymerizable with said monomer A, the B monomer being present in an amount of up to about 12% by weight of the total weight of all monomers, and (3) monomer C has the general formula X-Z wherein X is a group copolymerizable with said monomers A and B (preferably a vinyl group), and Z is a polymeric graft moiety having a Tg greater than 20° C., said moiety Z being essentially unreactive under copolymerization conditions, and wherein said group X of said monomer C and said monomers A and B are copolymerized to form a polymeric backbone chain having pendant therefrom graft polymeric moiety Z.

A graft polymeric moiety may be prepared as a macromer and copolymerized with one or more A and B monomers which form the backbone polymer such as acrylic acid, acrylamide, methacrylic acid, methacrylamide and alkyl acrylates where the alkyl groups contain from 1 to 14 carbon atoms (e.g., methyl, ethyl, propyl, isopropyl, butyl, amyl, hexyl, 2-ethylhexyl and other octyl, nonyl and decyl acrylates). See, for instance, the disclosure of U.S. Pat. No. 3,786,116, incorporated by reference in its entirety, in this regard.

Typical copolymerization techniques include but are not limited to conventional free radical initiated copolymerization techniques in the presence of a solvent. Suitable copolymerization temperatures range from about 20° C. to 150° C. for periods of time of from 2 to 24 hours until the desired degree of conversion occurs.

Upon completion of the polymerization process, the solvent is removed and a tacky acrylate copolymer results having an acceptable balance of tack and shear adhesive properties at high temperatures.

Depending upon the properties imparted to the backbone polymer as a result of the molecular weight of the particular graft employed, the resulting copolymer adhesive may need to be used in solution or emulsion form rather than as a melt adhesive. That is, if the molecular weight of the graft is sufficiently high, the resultant adhesive may be applied to a backing material or substrate in emulsion or solution form, with the water or solvent being removed upon application to the substrate.

With regard to the polymeric graft moiety portion of the adhesive composition, U.S. Pat. Nos. 3,786,116; 3,842,057; 3,842,058; 3,842,059; 3,862,098; 3,862,101, 3,862,102 and 4,554,324 disclose polymerizable macromers which are suitable for use as graft moieties on a backbone polymer as defined.

Preferably, the polymeric moiety Z is formed from a vinyl aromatic monomer such as styrene, alpha-methylstyrene, indene and p-tert-butylstyrene. However, the polymeric moiety Z may also be formed from vinyl toluene, acenaphthalene, acrylonitrile and methacrylonitrile; organic isocyanates including lower alkyl, phenyl, lower alkyl phenyl and halophenyl isocyanates; organic diisocyanates including lower alkylene, phenylene, and tolylene diisocyanates; lower alkyl and allyl acrylates and methacrylates, including methyl, t-butyl acrylates, and methacrylates; lower olefins, such as ethylene, propylene, butylene, isobutylene, pentene, hexene, etc.; vinyl esters of aliphatic carboxylic acids such as vinyl acetate, vinyl propionate, vinyl octoate, vinyl oleate, vinyl stearate, vinyl benzoate, vinyl lower alkyl ethers; conjugated dienes such as isoprene and butadiene; 2-oxazolines such as 2-ethyl-2-oxazoline; and vinyl unsaturated amides such as acrylamide, methylacrylamide, N,N-di(lower alkyl) acrylamides such as N,N-dimethylacrylamide.

The selection of the specific polymerizable monomer for the polymer graft is not critical, since as the above listing suggests, a wide variety of monomers (and the resulting polymeric moieties) can be used with success as a polymeric graft in the claimed composition.

A variety of functional groups may be employed to attach the graft Z to the polymer backbone.

Exemplary functional groups include but are not limited to

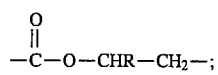

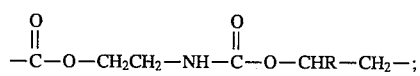

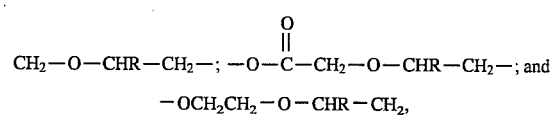

where R is a hydrogen atom or a lower alkyl group.

The molecular weight of the graft polymeric moiety must be sufficient to result in the formation of a "phase-separated" graft copolymer composition. Generally the molecular weight of the graft polymeric moiety will be within the range of from 2,000 to 60,000.

Preferably, the polymer graft is present in the copolymer in an amount of between 1.5 to 2.5 polymeric moieties per polymer backbone on average to enhance the high performance properties of the adhesive. See U.S. Pat. No. 5,352,516 in this regard, herein incorporated by reference.

The presence of the polymer graft on the backbone polymer in the manner stated has previously been found to result in a composition in which the respective polymeric backbone chains remain bound to one another at temperatures above the Tg of the backbone polymer. That is, the respective separate phases of the backbone polymers and the graft polymeric moieties are caused to be bound together without disadvantageously affecting the adhesive characteristics of the composition.

The percutaneous penetration enhancer employed has the ability to increase permeability of skin to transdermally administered pharmacologically active agents. Such enhancers are well-known in the art, and are discussed at length in U.S. Pat. Nos. 5,059,426 and 5,175,052, each herein incorporated by reference. By way of brief summary, such enhancers include but are not limited to surfactants (anionic, nonionic, cationic, zwitterionic), lipophilic solvents (terpenes, lactams), hydrophilic solvents (polyols, fatty acid esters, alcohols, sulfoxides), etc. Preferably, such enhancers are selected from the group consisting of sorbitols, ethoxylated alkyl phenols, gycerol, propylene glycol, polyethylene glycols, fatty acid esters, alcohols, and amines, and may be either water-soluble or non-water-soluble.

It has been found that the desirable adhesive properties of the graft-reinforced base polymers used in the present invention can be used with advantage upon admixture of percutaneous penetration enhancers with the base polymer to form a drug flux enhancer-tolerant pressure sensitive adhesive composition. That is, the enhancer can be admixed with the base polymer to maximize the ability of an incorporated pharmacologically active agent to be absorbed into the skin without adversely affecting the adhesive properties of the adhesive. Advantageously, it has been found that the percutaneous penetration enhancer can be used in amounts up to about 40 percent by weight, based on the weight of the composition, without adversely affecting the physical integrity of the adhesive or its adhesive properties. Preferably, the enhancer will be employed in an amount within the range of from 5 to 30 percent by weight, based on the weight of the composition.

The adhesive composition of the present invention may be used with advantage in a variety of conventional transdermal drug delivery devices. Such devices may take many forms. Generally, such devices comprise a backing material and an adhesive layer on at least a portion of the backing material. A release liner covers the adhesive layer until use at which time the liner is removed and the adhesive layer placed on the skin. The backing material is impermeable to the pharmacologically active agent. The pharmacologically active agent may be contained in either a liquid reservoir within the backing layer, within a matrix layer on said backing layer disposed between the adhesive layer and the backing layer, or within a layer of the drug flux enhancer-adhesive composition of the present invention. The manner of formulation of such various transdermal drug delivery systems is within the ability of one skilled in the art.

In order to demonstrate the advantageous properties of the adhesive compositions of the present invention, various polymeric adhesive compositions were prepared having the compositions described in the following Examples.

Examples 1–8 depict various phase-separated graft copolymers which may be employed in the composition of the present invention.

EXAMPLE 1

A polyacrylate polymer having a polystyrene graft having a molecular weight of 13,000 is prepared by the following method. In a glass 1 liter reaction vessel the following charge stock was incrementally polymerized under a nitrogen atmosphere at 73° C. over 5½ hours with agitation to a viscosity of 4300 centipoise:

| | |
|---|---|
| Isooctyl Acrylate (A monomer) | 134 grams |
| Acrylic Acid (B monomer) | 3 grams |
| Qm-824 (B monomer) | 25 grams |
| Vinyl Acetate (B monomer) | 20 grams |
| Acrylamide (B monomer) | 3.15 grams |
| Diacetone Acrylamide (B monomer) | 3.15 grams |
| Polystyrene Methacrylate Macromer (Graft) | 8.58 grams |
| Benzoyl Peroxide (Initiator) | .62 grams |
| Ethyl Acetate (Solvent) | 367 grams |

Note: Qm-824 is a Rohm & Haas product identified as β-Carboxyethyl Acrylate

EXAMPLE 2

A polyacrylate polymer having a polystyrene graft having a molecular weight of 20,000 is prepared by the method of Example 1 from the following charge stock:

| | |
|---|---|
| Isooctyl Acrylate | 134 grams |
| Acrylic Acid | 3 grams |
| Qm-824 | 25 grams |
| Vinyl Acetate | 20 grams |
| Acrylamide | 3.15 grams |
| Diacetone Acrylamide | 3.15 grams |
| Polystyrene Methacrylate Macromer | 14.39 grams |
| Benzoyl Peroxide | .64 grams |
| Ethyl Acetate | 378 grams |

EXAMPLE 3

A polyacrylate polymer solution having a viscosity of 2,200 cps and having a polystyrene graft having a molecular weight of 30,000 is prepared by the method of Example 1 from the following charge stock:

| | |
|---|---|
| Isooctyl Acrylate | 134 grams |
| Acrylic Acid | 3 grams |
| Qm-824 | 25 grams |
| Vinyl Acetate | 20 grams |
| Acrylamide | 3.15 grams |
| Diacetone Acrylamide | 3.15 grams |
| Polystyrene Methacrylate Macromer | 19.8 grams |
| Benzoyl Peroxide | .65 grams |
| Ethyl Acetate | 388 grams |

EXAMPLE 4

A polyacrylate polymer solution having a viscosity of 200,000 cp and having a polystyrene graft having a molecular weight of 47,000 is prepared by the method of Example 1 from the following charge stock:

| | |
|---|---|
| Isooctyl Acrylate | 134 grams |
| Acrylic Acid | 3 grams |
| Qm-824 | 25 grams |
| Vinyl Acetate | 20 grams |
| Acrylamide | 3.15 grams |
| Diacetone Acrylamide | 3.15 grams |
| Polystyrene Methacrylate Macromer | 30 grams |
| Benzoyl Peroxide | .64 grams |
| Ethyl Acetate | 372 grams |

EXAMPLE 5

A polyacrylate polymer solution having a viscosity of 4,700 cps after dilution with 150 grams of ethyl acetate and having a polystyrene graft having a molecular weight of 54,000 is prepared by the method of Example 1 from the following charge stock:

| | |
|---|---|
| Isooctyl Acrylate | 134 grams |
| Acrylic Acid | 3 grams |
| Qm-824 | 25 grams |
| Vinyl Acetate | 20 grams |
| Acrylamide | 3.15 grams |
| Diacetone Acrylamide | 3.15 grams |
| Polystyrene Methacrylate Macromer | 35.64 grams |
| Benzoyl Peroxide | .62 grams |
| Ethyl Acetate | 368 grams |

EXAMPLE 6

A polyacrylate polymer solution having a viscosity of 11,600 cps and having a poly-alpha-methylstyrene graft having a molecular weight of 6,600 is prepared by the method of Example 1 from the following charge stock:

| | |
|---|---|
| Isooctyl Acrylate | 66.4 grams |
| Acrylic Acid | 1.48 grams |
| Qm-824 | 12.34 grams |
| Vinyl Acetate | 9.87 grams |
| Acrylamide | 1.55 grams |
| Diacetone Acrylamide | 1.55 grams |
| Poly Alpha-Methyl Styrene Macromer | 2.62 grams |
| Benzoyl Peroxide | .31 grams |
| Ethyl Acetate | 181.4 grams |

EXAMPLE 7

A polyacrylate polymer solution having a viscosity of 18,000 cps and having a poly-alpha-methylstyrene graft having a molecular weight of 12,100 is prepared by the method of Example 1 from the following charge stock:

| | |
|---|---|
| Isooctyl Acrylate | 51.1 grams |
| Acrylic Acid | 1.14 grams |
| Qm-824 | 9.5 grams |
| Vinyl Acetate | 7.6 grams |
| Acrylamide | 1.2 grams |
| Diacetone Acrylamide | 1.2 grams |
| Poly Alpha-Methyl Styrene Macromer | 3.26 grams |
| Benzoyl Peroxide | .24 grams |
| Ethyl Acetate | 139.7 grams |

EXAMPLE 8

A polyacrylate polymer having a viscosity of 1,750 cps and having a poly-alpha-methylstyrene graft having a molecular weight of 30,000 is prepared by the method of Example 1 from the following charge stock:

| | |
|---|---|
| Isooctyl Acrylate | 53.8 grams |
| Acrylic Acid | 1.2 grams |
| Qm-824 | 10 grams |
| Vinyl Acetate | 8 grams |
| Acrylamide | 1.26 grams |
| Diacetone Acrylamide | 1.26 grams |
| Poly Alpha-Methyl Styrene Macromer | 7.92 grams |
| Benzoyl Peroxide | .26 grams |
| Ethyl Acetate | 88.6 grams |
| Toluene | 59 grams |

When the polymers described above are mixed with the percutaneous penetration enhancers, viscoelastics properties are obtained in accordance with the desired limits. Once formulated, the adhesives can be attached to any number of substrate materials (such as skin) by conventional means.

When mixed with the desired enhancer at the appropriate level, the resulting viscoelastic properties are such that the material is pressure sensitive and exhibits good long term skin adhesion. The basis for evaluation of the viscoelastic characteristics of the resulting enhancer/polymer composition is the determination of storage modulus (G'), loss modulus (G"), and tan delta values via dynamic mechanical analysis in a frequency range of from 0.01 to 100 rad/sec. Desirable defining parameters for long term skin adhesion are: G' at 0.01 rad/sec of from $5 \times 10^3$ dynes/cm$^2$ to $1 \times 10^6$ dynes/cm$^2$, and a tan delta at 0.01 rad/sec of from 0.3 to 0.8.

The following samples will serve to illustrate the versatility of these adhesive systems.

EXAMPLE 9

A polyacrylate base polymer having a polystyrene graft of molecular weight of 20,000 is prepared by the method of Example 1 from the following charge stock:

| | |
|---|---|
| Isooctyl Acrylate | 275.3 grams |
| CD 504 | 57.4 grams |
| Polystyrene Macromer | 16.4 grams |
| Hydroxypropyl Methacrylate | 32.5 grams |
| Benzoyl Peroxide | 0.94 grams |
| Ethyl Acetate | 439 grams |

Note: CD 504 is a polyethoxylated monomer available from Sartomer

The thus-formed polyacrylate is then mixed with 20.1 grams of isopropyl myristate as a percutaneous penetration enhancer.

A sample is prepared by casting the solution onto a siliconized PET release sheet to a wet film thickness of 24 mils, and dried in a 150° F. oven until no solvent remains. The dried adhesive is then folded upon itself until a slab of 1.0 to 1.5 mm thickness and having no obvious flaws is obtained.

The slab is then tested via dynamic mechanical analysis on a Rheometrics RAA DMA using a 12.5 mm disk arranged in a parallel plate configuration. The sample is tested using a frequency range of from 0.01 to 100 rad/sec, and 1% strain.

The sample is measured to have a G' at 0.01 rad/sec of $1.2 \times 10^4$ dynes/cm$^2$ and a tan delta at 0.01 rad/sec of 0.4.

EXAMPLE 10

The base polymer of Example 9 is mixed with 20.1 grams of N,N-Diethyl m-Toluamide (DEET) as penetration enhancer.

A sample is prepared and tested as per Example 9 with the measured G' at 0.01 rad/sec being $4.5 \times 10^4$ dynes/cm$^2$ with a tan delta of 0.3.

EXAMPLE 11

The base polymer of Example 9 is mixed with 20.1 grams lauryl alcohol as penetration enhancer.

A sample is prepared and tested as per Example 9 with the measured G' at 0.01 rad/sec being $3.6 \times 10^4$ dynes/cm$^2$ with a tan delta of 0.30.

EXAMPLE 12

A polymeric base polymer having a polystyrene graft of molecular weight 20,000 is prepared as in Example 1 from the following charge stock:

| | |
|---|---|
| Isooctyl Acrylate | 77.8 grams |
| Acrylic Acid | 1.8 grams |
| Acrylamide | 1.9 grams |
| Diacetone Acrylamide | 1.9 grams |
| Polystyrene Macromer | 5.5 grams |
| Vinyl Acetate | 12.1 grams |
| Ethyl Acetate | 154.0 grams |
| Benzoyl Peroxide | 0.4 grams |

The base polymer is then mixed with 25.3 grams of DEET as penetration enhancer.

A sample is prepared and tested as per Example 9 with the measured G' at 0.01 rad/sec being $1.0 \times 10^5$ dynes/cm$^2$ with a tan delta of 0.32.

EXAMPLE 13

The base polymer of Example 12 is prepared and mixed with 43.0 grams of DEET as penetration enhancer.

A sample is prepared and tested as per Example 9, with the measured G' at 0.01 rad/sec being $4.6 \times 10^4$ dynes/cm$^2$ with a tan delta of 0.3.

EXAMPLE 14

The base polymer of Example 12 is prepared and mixed with 25.3 grams of lauryl alcohol as penetration enhancer.

A sample is prepared and tested per Example 9 with the measured G' at 0.01 rad/sec being $5.9 \times 10^4$ dynes/cm$^2$ with a tan delta of 0.39.

EXAMPLE 15

The base polymer of Example 12 is prepared and mixed with 25.3 grams of polysorbate 80 as penetration enhancer.

A sample is prepared and tested per Example 9 with the measured G' at 0.01 rad/sec being $7.6 \times 10^4$ dynes/cm$^2$ with a tan delta of 0.31.

EXAMPLE 16

The base polymer of Example 12 is prepared and mixed with 43.0 grams of isopropyl myristate as penetration enhancer.

A sample is prepared and tested per Example 9 with the measured G' at 0.01 rad/sec being $3.1 \times 10^4$ dynes/cm$^2$ with a tan delta of 0.41.

The pharmacologically active agent to be administered by use of the transdermal drug delivery mens is employed in a conventional manner. Suitable active agents include those that are compatible with the administration system of the present invention and exhibit the expected benefit upon percutaneous administration. Such active agents include, without limitation, antiinflammatory drugs, bacteriostatic agents, antifungal agents, coronary vasodilators, etc. Exemplary of the most commonly transdermally-administered active agents are clonidine, estrodiol, nicotine, nitroglycerine and scopolamine, each commercially available in transdermal devices. See U.S. Pat. No. 5,372,819, herein incorporated by reference, for a more detailed discussion of suitable percutaneous administered active agents.

What is claimed is:

1. In a transdermal delivery system for administering at least one pharmacologically active agent comprising a flexible backing material impermeable to said active agent and an adhesive layer on at least a portion of said backing material, the improvement wherein said adhesive layer comprises a pressure sensitive adhesive composition comprised of (1) a percutaneous penetration enhancer to increase permeability of skin to transdermally administered pharmacologically active agents in admixture with (2) a macromer reinforced base polymer, said base polymer component comprising a phase separated graft copolymer comprised of copolymerized monomers A and B to form a backbone polymer having polymeric moieties grafted thereto, wherein monomer A is a monomeric acrylic or methacrylic ester of a non-tertiary alcohol having from 1 to 14 carbon atoms, with the average number of carbon atoms being in the range of about 4 to 12, and monomer B is a polar monomer which is copolymerizable with monomer A, said percutaneous penetration enhancer being present in said composition in an amount of up to 40 percent by weight based on the weight of the composition.

2. The delivery system of claim 1 wherein said percutaneous penetration enhancer is selected from the group consisting of sorbitols, ethoxylated alkyl phenols, gycerol, propylene glycol, polyethylene glycols, fatty acid esters, alcohols, and amines.

3. The delivery system of claim 1 wherein said percutaneous penetration enhancer has a molecular weight of from 20 to 20,000.

4. The delivery system of claim 1 wherein said graft polymeric moiety is a polymerized monoalkenyl-substituted aromatic hydrocarbon.

5. The delivery system of claim 4 wherein said polymerized monoalkenyl-substituted aromatic hydrocarbon comprises polystyrene.

6. The delivery system of claim 1 wherein the molecular weight of said graft polymeric moiety is in the range of from about 30,000 to 60,000.

7. The delivery system of claim 1 wherein the graft polymeric moiety is present in an amount of from 1.5 to 2.5 graft moieties per polymer backbone chain on average.

8. The delivery system of claim 7 wherein said graft polymeric moiety is present in an amount of about 2 polymeric moieties per polymeric backbone chain on average.

9. The delivery system of claim 1 wherein said B monomer is selected from the group consisting of acrylic acid, methacrylic acid, itaconic acid, acrylamide, methylacrylamide, acrylonitrile, methacrylonitrile, diacetone acrylamide and 2-carboxyl ethyl esters of acrylic acid.

10. The delivery system of claim 1 wherein said base polymer comprises from about 50 to 80 percent by weight of said A monomer.

11. The delivery system of claim 10 wherein said base polymer comprises from about 50 to 65 percent by weight of said A monomer.

12. The delivery system of claim 1 wherein said A monomer comprises an ester of acrylic and methyacrylic acid with a non-tertiary alcohol selected from the group consisting of 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, 1-dodecanol, etc.

13. The delivery system of claim 1 wherein said graft polymeric moiety comprises poly-alpha-methylstyrene.

14. The delivery system of claim 13 wherein said poly-alpha-methylstyrene has a molecular weight of at least 12,000.

15. The delivery system of claim 1 wherein said percutaneous penetration enhancer is present in said composition in an amount in the range of from 5 to 30 percent by weight.

* * * * *

Adverse Decision In Interference

Patent No. 5,573,778, Donald J. Therriault, Kenneth W. Rodgers, DRUG FLUX ENHANCER-TOLERANT PRESSURE SENSITIVE ADHESIVE COMPOSITION, Interference No. 104,263, final judgment adverse to the patentees rendered December 10, 2003, as to claims 1-15.

*(Official Gazette August 10, 2004)*